United States Patent
Zhou et al.

(10) Patent No.: US 8,699,020 B1
(45) Date of Patent: Apr. 15, 2014

(54) HANDHELD RAMAN SPECTROMETER

(71) Applicants: Xin Jack Zhou, Hockessin, DE (US); Daoguo Jiang, Shanghai (CN); Sean Xiaolu Wang, Wilmington, DE (US)

(72) Inventors: Xin Jack Zhou, Hockessin, DE (US); Daoguo Jiang, Shanghai (CN); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 0 days.

(21) Appl. No.: 13/711,668

(22) Filed: Dec. 12, 2012

Related U.S. Application Data

(60) Provisional application No. 61/576,376, filed on Dec. 16, 2011.

(51) Int. Cl.
*G01J 3/44* (2006.01)

(52) U.S. Cl.
USPC ........................................................ 356/301

(58) Field of Classification Search
USPC ............................................ 356/301, 72–73
See application file for complete search history.

(56) References Cited

U.S. PATENT DOCUMENTS

| | | | |
|---|---|---|---|
| 7,245,369 B2 | 7/2007 | Wang et al. | |
| 7,524,671 B2 | 4/2009 | Clarke et al. | |
| 7,542,138 B2 | 6/2009 | Gardner, Jr. | |
| 7,675,611 B2 | 3/2010 | Azimi et al. | |
| 7,928,391 B2 | 4/2011 | Azimi et al. | |
| 2011/0191272 A1* | 8/2011 | McGuire | 706/11 |
| 2012/0033290 A1* | 2/2012 | Achtenhagen et al. | 359/320 |
| 2012/0223130 A1* | 9/2012 | Knopp et al. | 235/375 |

\* cited by examiner

*Primary Examiner* — Tarifur Chowdhury
*Assistant Examiner* — Abdullahi Nur

(57) ABSTRACT

This invention discloses a handheld Raman spectrometer. The handheld Raman spectrometer comprises: (i) a handheld enclosure; (ii) a volume Bragg grating stabilized laser mounted in the handheld enclosure for producing laser light; (iii) a Raman probe for delivering the laser light to a subject to produce Raman scattered light from the subject and collecting the Raman scattered light; (iv) a spectrometer mounted in the handheld enclosure for measuring the Raman scattered light and obtaining a Raman spectrum; (v) a high brightness display mounted in the handheld enclosure for displaying the obtained Raman spectrum; (vi) a multi-touch screen mounted on top of the high brightness display for receiving user inputs; (vii) a central processing unit mounted in the handheld enclosure for processing user inputs and controlling operation of the handheld Raman spectrometer; and (viii) a user interface based on the high brightness display, the multi-touch screen, and the central processing unit, the user interface is programmed to be capable to respond to user inputs incurring at least two points of contact with the multi-touch screen.

7 Claims, 1 Drawing Sheet

HANDHELD RAMAN SPECTROMETER

REFERENCE TO RELATED APPLICATION

This application claims an invention which was disclosed in Provisional Patent Application No. 61/576,376, filed Dec. 16, 2011, entitled "HANDHELD RAMAN SPECTROMETER". The benefit under 35 USC §119(e) of the above mentioned United States Provisional Applications is hereby claimed, and the aforementioned applications are hereby incorporated herein by reference.

FIELD OF THE INVENTION

This invention generally relates to a Raman spectrometer, and more specifically to a handheld Raman spectrometer.

BACKGROUND

Raman spectroscopy has been demonstrated as a powerful non-invasive analytical technology for material characterization and identification. Conventional Raman spectrometers suffer from a bulky size, which limits them only to laboratory usages. Recently, with the development of diode laser based excitation light sources and compact CCD (charge-coupled device) array spectrometers, Raman spectrometers were made as compact handheld instruments that can be used to perform in-field sample analysis. Some exemplary handheld Raman spectrometers can be found in U.S. Pat. No. 7,542,138 to Gardner, Jr., U.S. Pat. No. 7,675,611 to Azimi et al., U.S. Pat. No. 7,928,391 to Azimi et al., and U.S. Pat. No. 7,524,671 to Clarke et al.

However, existing handheld Raman instruments lack certain features which are important for in-field operations. Such features include but are not limited to (i) bright display unit working in all light conditions; (ii) convenient way for user command and data entry; (iii) interactive guidance to help the user perform spectrum measurement and analysis; (iv) enhanced battery life; and (v) remote control capability.

SUMMARY OF THE INVENTION

It is thus the overall goal of the present invention to provide a handheld Raman spectrometer which is fully optimized for in-field usages. The handheld Raman spectrometer comprises: (i) a handheld enclosure; (ii) a volume Bragg grating stabilized laser mounted in the handheld enclosure for producing laser light; (iii) a Raman probe for delivering the laser light to a subject to produce Raman scattered light from the subject and collecting the Raman scattered light; (iv) a spectrometer mounted in the handheld enclosure for measuring the Raman scattered light and obtaining a Raman spectrum; (v) a high brightness display mounted in the handheld enclosure for displaying the obtained Raman spectrum; (vi) a multi-touch screen mounted on top of the high brightness display for receiving user inputs; (vii) a central processing unit mounted in the handheld enclosure for processing user inputs and controlling operation of the handheld Raman spectrometer; and (viii) a user interface based on the high brightness display, the multi-touch screen, and the central processing unit, the user interface is programmed to be capable to respond to user inputs incurring at least two points of contact with the multi-touch screen.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
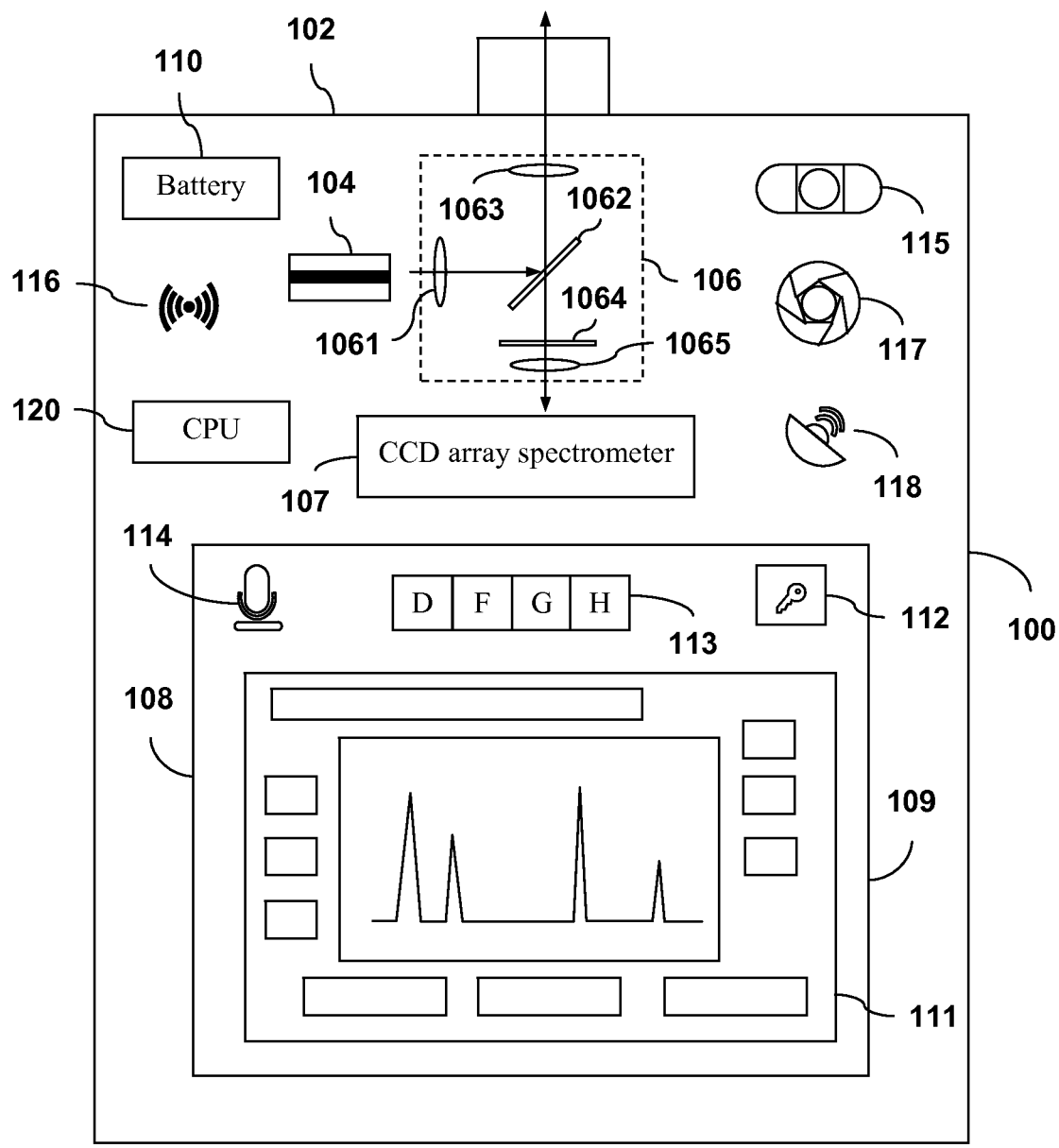
FIG. 1 is a block diagram of one exemplary embodiment of the handheld Raman spectrometer.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a handheld Raman spectrometer. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

A block diagram of one exemplary embodiment of the handheld Raman spectrometer is shown in FIG. 1. The handheld Raman spectrometer 100 comprises a handheld enclosure 102. All the optical, mechanical, and electronic components of the Raman spectrometer are contained in the handheld enclosure 102 to form a field operable instrument. A central processing unit (CPU) 120 is employed for processing user inputs and controlling the operation of the Raman spectrometer. All the active components of the Raman spectrometer 100 are powered by a high capacity rechargeable battery 110.

The optical components of the Raman spectrometer include a diode laser 104 as the excitation light source. The diode laser 104 is preferably a 785 nm near-infrared (NIR) laser with its output wavelength and spectral linewidth stabilized and narrowed with a volume Bragg grating as disclosed in U.S. Pat. No. 7,245,369, which is hereby incorporated herein by reference. The handheld Raman spectrometer 100 further comprise a Raman probe 106 for laser light delivery and Raman scattering signal collection, which is optimized to take full advantage of the high spectral and spatial brightness of the laser source. The Raman probe 106 comprises a first optical lens 1061 to collect and collimate the laser light. The collimated laser light is then reflected by a dichroic filter 1062 to a second optical lens 1063. The second optical lens 1063 focuses the laser light onto the subject sample (not shown) to stimulate Raman scattering from the subject sample. The high spatial brightness of the volume Bragg grating stabilized laser 104 makes it possible to focus the laser beam into a small spot for efficient Raman scattering excitation. The second optical lens 1063 also features a large numerical aperture for efficient collection of the Raman scattering signal. The collected Raman scattering signal is collimated by the second optical lens 1063 and passes through the dichroic filter 1062 for filtering out the Rayleigh scattering and the reflected laser light. A longpass edge filter 1064 following the dichroic filter 1062 is used to further remove the Rayleigh scattering from the Raman scattering signal. The filtered Raman scattering signal is focused by a third optical lens 1065 and delivered into a CCD array spectrometer 107 for spectral analysis.

The handheld Raman spectrometer 100 further comprises a high brightness display 108 and a multi-touch screen 109. The high brightness display 108 is preferably an organic light emitting diode (OLED) display, which works without a backlight. Thus, it can display deep black levels and can be thinner and lighter than liquid crystal displays (LCDs). The OLED display 108 offers fast response time, wide viewing angle, good color reproduction, outstanding contrast level, and high brightness, which enable it to be used in both low and high ambient light conditions. In addition, the OLED display 108 features extremely low power consumption to enhance the battery life of the handheld Raman spectrometer 100. The multi-touch screen 109 is preferably a capacitive touch screen, which offers 90 percent light transmittance versus only 75 percent for a resistive touch-screen. This further improves the brightness of the display unit.

The multi-touch capability of the capacitive touch screen 109 makes it possible to recognize the presence of two or more points of contact with the screen surface. This capability enables a more interactive and friendly user interface 111 to be constructed with the assistance of the high brightness display 108, the multi-touch screen 109, and the central processing unit 120.

The user interface 111 is programmed to be capable to respond to user inputs incurring at least two points of contact with the multi-touch screen to realize advanced functionality such as pinch to zoom or to activate predefined programs. As one example, an interactive user guide is provided in the user interface 111 by incorporating an assistance icon 112 on the upper right corner of the touch screen display. When the user meets some problem during the measurement process, he or she can pinch out the assistance icon 112 such that an animation or movie clip is displayed to illustrate what the user should do in the next step. If the user has some question about a specific function or parameter on the user interface 111, he or she can tap on the assistance icon 112 and in the meantime tap on the subject portion of the user interface 111. A description about the function or parameter will be displayed accordingly. Such a real-time assistance is extremely useful for field operations where customer support is generally unavailable. The capacitive touch-screen 109 also enables other functions for the user interface 111 such as swiping through file lists, zooming in and out of a spectrum, typing spectral descriptions and messages, and scrolling through user menus.

Due to size limitation of the handheld Raman spectrometer, the touch screen 109 has a limited space for user command and data entry. To solve this problem, an enlarged virtual keyboards 113 is used which displays only a few characters instead of the whole character set. The user swipes over the keyboard to switch the displayed characters. When the desired character appears, the user may tap on the character or swipe over it in another direction to enter the character. Alternatively, a voice entry system is provided. By tapping on a microphone icon 114, the microphone of the Raman spectrometer is turned on to receive the user's verbal command. The verbal command is then recognized and compared to a set of standard commands for spectrum measurement and analysis. A list of mostly matched commands is then displayed for the user to select from. Data entry for spectrometer settings, such as laser power, integration time, etc. can be performed in a similar manner. In addition to the voice entry system, the handheld Raman spectrometer may be equipped with a capacitive stylus pen (not shown) to assist the user to perform data and text entry via virtual keyboards or through handwriting and character recognition. To further reduce the burden of data entry, the handheld Raman spectrometer is equipped with a barcode scanner 115 to read the identification data of samples with barcode identifiers. The measured Raman spectrum of the sample is then associated with its identification data for categorization purposes.

The handheld Raman spectrometer 100 further comprises a wireless communication module 116. Through the wireless communication module 116, the handheld Raman spectrometer 100 may transmit the obtained Raman spectrum to a central office to be analyzed and compared with a spectrum database such that the subject sample is identified. This approach allows the spectrum database to be stored in the central office instead of in the Raman spectrometer itself, thus saving a substantial amount of memory space. In addition, the handheld Raman spectrometer 100 can be remotely controlled through wireless communication with a remote control unit (not shown). Some examples of the remote control unit include tablet computers or smart phones. In cases where the subject sample contains hazardous or explosive material or the adjacent environment of the subject is dangerous for human operators, the user may remotely operate the Raman spectrometer (firing the laser, collecting the Raman spectrum, etc.) through the remote control unit. To monitor the status of the subject sample, the handheld Raman spectrometer may be equipped with an imaging sensor 117 (e.g. a digital camera) to take images of the subject sample and send the images to the remote control unit through the wireless communication module 116.

The handheld Raman spectrometer further comprises a positioning sensor 118, such as a GPS (global positioning system) sensor for acquiring its geographic location. The obtained geographic location can be reported to a central office such that the Raman spectrum of the subject sample is associated with its geographic location. Such a feature is extremely useful for industrial process control, where a plurality of Raman spectrometers are employed for monitoring the manufacturing process. When an abnormal Raman spectrum is detected, the central office can quickly locate the related subject by using the positioning sensor 118.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A handheld Raman spectrometer, comprising:
a handheld enclosure;
a volume Bragg grating stabilized laser mounted in the handheld enclosure for producing laser light;
a Raman probe for delivering the laser light to a subject to produce Raman scattered light from the subject and collecting the Raman scattered light;
a spectrometer mounted in the handheld enclosure for measuring the Raman scattered light and obtaining a Raman spectrum;
an imaging sensor mounted in the handheld enclosure for taking images of the subject;
a wireless communication module mounted in the handheld enclosure for receiving commands from a remote control unit and sending the Raman spectrum and images of the subject to the remote control unit;
a high brightness display mounted in the handheld enclosure for displaying the Raman spectrum;
a multi-touch screen mounted on top of the high brightness display for receiving user inputs;
a central processing unit mounted in the handheld enclosure for processing the user inputs and controlling operation of the handheld Raman spectrometer in accordance to the user inputs and the commands from the remote control unit; and
a user interface based on the high brightness display, the multi-touch screen, and the central processing unit, said user interface is programmed to be capable to respond to user inputs incurring at least two points of contact with the multi-touch screen.

2. The handheld Raman spectrometer of claim 1, wherein the high brightness display comprises an organic light emitting diode (OLED) display.

3. The handheld Raman spectrometer of claim 1, wherein the multi-touch screen comprises a capacitive touch screen.

4. The handheld Raman spectrometer of claim 1, wherein the user interface comprises an interactive user guide for providing real-time assistance to a user.

5. The handheld Raman spectrometer of claim 1, further comprising a barcode scanner mounted in the handheld enclosure.

6. The handheld Raman spectrometer of claim 1, further comprising a positioning sensor mounted in the handheld enclosure.

7. The handheld Raman spectrometer of claim 1, further comprising a voice entry system.

* * * * *